(12) United States Patent
Fecher et al.

(10) Patent No.: US 9,737,465 B2
(45) Date of Patent: Aug. 22, 2017

(54) PROCESS FOR PRODUCING A BLANK, AND A BLANK

(71) Applicant: DENTSPLY INTERNATIONAL INC., York, PA (US)

(72) Inventors: Stefan Fecher, Johannesberg (DE); Heiner Hörhold, Büdingen (DE); Udo Schusser, Alzenau (DE); Markus Vollmann, Gelnhausen (DE); Martin Kutzner, Neuberg (DE)

(73) Assignee: DENTSPLY INTERNATIONAL INC., York, PA (US)

( * ) Notice: Subject to any disclaimer, the term of this patent is extended or adjusted under 35 U.S.C. 154(b) by 0 days.

(21) Appl. No.: 14/892,369

(22) PCT Filed: Apr. 30, 2014

(86) PCT No.: PCT/EP2014/058920
§ 371 (c)(1),
(2) Date: Nov. 19, 2015

(87) PCT Pub. No.: WO2014/177659
PCT Pub. Date: Nov. 6, 2014

(65) Prior Publication Data
US 2016/0113845 A1    Apr. 28, 2016

(30) Foreign Application Priority Data
May 3, 2013  (DE) .................. 10 2013 104 561

(51) Int. Cl.
*C03C 10/04*        (2006.01)
*A61K 6/027*        (2006.01)
(Continued)

(52) U.S. Cl.
CPC ........ *A61K 6/0273* (2013.01); *A61C 13/0022* (2013.01); *A61K 6/024* (2013.01);
(Continued)

(58) Field of Classification Search
CPC ............ C03C 10/0009; C03C 10/0018; C03C 10/0027
(Continued)

(56) References Cited

U.S. PATENT DOCUMENTS 6,455,451 B1 *  9/2002  Brodkin ................. A61K 6/033
                                                          106/35
6,517,623 B1 *  2/2003  Brodkin ................. C03B 19/06
                                                          106/35
(Continued)

FOREIGN PATENT DOCUMENTS

DE    102010056037 A1    6/2012
EP        1484031 A1    12/2004
(Continued)

*Primary Examiner* — Noah Wiese
(74) *Attorney, Agent, or Firm* — David A. Zdurne; Douglas J. Hura; Leana Levin

(57) ABSTRACT

The invention relates to a blank for producing a dental molded part such as an inlay, onlay, crown or bridge, and to a method for producing the blank. To be able to machine a dental molded part, in particular one having thin wall thicknesses, from the blank without difficulty, the blank is designed to consist of a glass ceramic having a density of between 30 and 60% of theoretical density, and of glass-ceramic powder particles with a particle size distribution $d_{90} \leq 80$ μm, lithium silicate crystals being present in an amount of 10 to 90% by volume.

24 Claims, 1 Drawing Sheet

| Phase | Change points | | Pressure Increase/Decrease [MPa/sec] | Holding time |
|---|---|---|---|---|
| | Pressure 1 [MPa] | Pressure 2 [MPa] | | |
| 1 | 0 | 30 | 15 | |
| 2 | 30 | 200 | 100 | |
| 3 | 200 | 200 | | 10 |
| 4a | 200 | 20 | 40 | |
| 4b | 20 | 0 | 10 | |

Example of pressurization during pressing.

(51) Int. Cl.
  *A61C 13/00* (2006.01)
  *C03C 4/00* (2006.01)
  *C03C 10/00* (2006.01)
  *C03B 32/02* (2006.01)
  *C03B 19/06* (2006.01)
  *C03B 19/10* (2006.01)
  *C03B 32/00* (2006.01)
  *C03C 3/097* (2006.01)
  *A61K 6/02* (2006.01)

(52) U.S. Cl.
  CPC .......... *C03B 19/06* (2013.01); *C03B 19/1005* (2013.01); *C03B 19/1055* (2013.01); *C03B 19/1095* (2013.01); *C03B 32/00* (2013.01); *C03B 32/02* (2013.01); *C03C 3/097* (2013.01); *C03C 4/0021* (2013.01); *C03C 10/0027* (2013.01)

(58) Field of Classification Search
  USPC .......................................... 501/5, 7
  See application file for complete search history.

(56) References Cited

U.S. PATENT DOCUMENTS

| | | | |
|---|---|---|---|
| 6,984,261 B2* | 1/2006 | Cummings | A61K 6/0276 106/35 |
| 9,241,879 B2* | 1/2016 | Castillo | A61K 6/0094 |
| 2003/0073563 A1* | 4/2003 | Brodkin | C03B 19/06 501/5 |
| 2005/0098064 A1* | 5/2005 | Schweiger | C03C 10/0027 106/35 |
| 2008/0120994 A1 | 5/2008 | Schweiger et al. | |
| 2012/0309607 A1 | 12/2012 | Durschang et al. | |
| 2013/0295523 A1 | 11/2013 | Durschang et al. | |
| 2014/0120297 A1 | 5/2014 | Reinshagen et al. | |
| 2014/0225290 A1 | 8/2014 | Ritzberger et al. | |

FOREIGN PATENT DOCUMENTS

| | | |
|---|---|---|
| WO | 2011076422 A1 | 6/2011 |
| WO | 2012059143 A1 | 5/2012 |
| WO | 2012080513 A1 | 6/2012 |
| WO | 2013053865 A2 | 4/2013 |

* cited by examiner

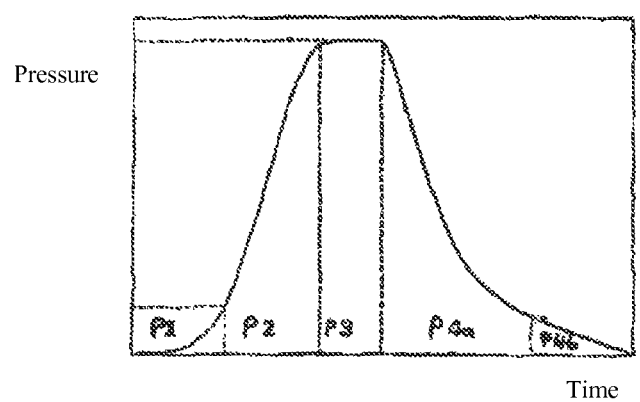
| Phase | Change points | | Pressure Increase/Decrease [MPa/sec] | Holding time |
|---|---|---|---|---|
| | Pressure 1 [MPa] | Pressure 2 [MPa] | | |
| 1 | 0 | 30 | 15 | |
| 2 | 30 | 200 | 100 | |
| 3 | 200 | 200 | | 10 |
| 4a | 200 | 20 | 40 | |
| 4b | 20 | 0 | 10 | |
Example of pressurization during pressing.

PROCESS FOR PRODUCING A BLANK, AND A BLANK

The invention relates to a blank for producing a dental molded part, such as an inlay, an onlay, a crown, or a bridge, whereby the blank contains a lithium silicate crystal fraction of more than 10% by volume.

The invention further relates to a process for producing a dental molded part, such as an inlay, an onlay, a crown, or a bridge. The invention also relates to a monolithic dental molded part.

WO 2012/080513 A1 discloses a process for producing dental molded parts from porous glass, which does not contain a crystalline contingent. The density of the blank is in the range between 50% and 95% of the theoretical density of a fully sintered blank. The corresponding blanks are used to produce monolithic dental molded parts such as crowns, partial crowns, bridges, inlays or onlays by means of milling, whereby dry machining is employed.

WO 2011076422 A1 and WO 2012/059143 A1 describe lithium silicate glass ceramics that are used in the manufacture of dental molded parts. The corresponding glass ceramics reportedly have good mechanical and optical properties.

Known from WO 2013/053865 A2 is a blank composed of lithium silicate glass ceramics, from which are produced dental molded parts. The ceramic mandatorily contains a trivalent metal oxide selected from the group $Y_2O_3$, $La_2O_3$, $Yb_2O_3$, $Bi_2O_3$ and mixtures thereof. Furthermore, the glass ceramic is essentially free of $K_2O$ and $Na_2O$.

In the manufacture of dental prostheses based on lithium silicate glass ceramics it is also known in the art to produce cylindrical pellets and to subsequently press these in a muffle (EP 1 484 031 B1).

The objective of the present invention is to produce a blank, from which a dental molded part can be worked out without any problems. In this, it should be possible to realize thin wall thicknesses. Machining should be possible with only minimum tool wear. Furthermore, the dental molded parts produced from the blank should contain favourable mechanical characteristics.

At least one of the problem aspects mentioned above is solved with respect to a blank for producing a dental molded part, such as inlay, onlay, crown, or bridge, by stipulating that the blank consists of a glass ceramic with a density of between 30% and 60% of the theoretical density of the fully sintered blank and of glass-ceramic powder particles with a grain size distribution $d_{90} \leq 80$ μm, in particular a grain size distribution $d_{50}$ of between 10 μm and 60 whereby the proportion of lithium silicate crystals is between 10% by volume and 90% by volume.

A blank of this type is machined by milling, whereby it has surprisingly been noted that tool wear is low so that expensive tools, e.g. diamond-tipped ones, are not required. Once dental moulded parts worked out of such a blank have been sintered to completion, one also surprisingly notices a high rigidity, whereby in comparison to a dental prosthesis worked out of a blank that has been sintered to completion, one obtains an increase in rigidity of between 10% and 50%. In particular this provides the option of achieving structures with thin walls that are not destroyed during sintering to completion, since the blanks possess sufficient stability on account of the crystalline phase fraction.

This also offers the advantage that no aids such as support structures or a filling of cavities are required when sintering to completion.

In particular it is intended that the crystalline content of the blank is 30% by volume to 60% by volume. The blank further is characterized by possessing an open porosity of between 50% by volume and 60% by volume, more preferably between 20% by volume and 50% by volume.

The chosen parameter settings ensure that during the machining, which in particular is performed dry, it is possible to achieve an adequate surface smoothness, so that finishing work after the sintering is not necessarily required.

The glass-ceramic powder preferably should possess a grain size distribution $d_{50} \leq 25$ μm.

The grain size distribution as well as the pore size of 0.1 μm to 5 μm result in a dense packing of the powder particles in the blank, so that fine edge structures can easily be formed. No grains torn from the worked surface were visually detected.

In order to achieve the small pore size in the range between 0.1 μm to 5 μm, it is in particular intended that the fraction of fine glass particles is correspondingly high.

In particular it is intended that the blank possesses a disk-, cube-, or rod-like geometry, from which to the desired extent and in dependence on the size of the blanks one can produce one or several dental molded parts. For the purpose of clamping the blank into a milling machine it is intended that means originate from the circumferential surface, extending diametrically with respect to the centre of gravity of the blank, which may be used to fix the blank in position. One option is to lathe recesses into the blank, into which engage fixing means originating from the processing machine. Alternatively, it is possible to attach, e.g. glue, adapters to the circumferential surface, which are intended to act as holders in a processing machine. Another option is to create protrusions on the blank, which then can serve as mounts.

In particular, the invention is characterized by a blank of glass-ceramic powder particles with a composition (in % by weight) having:

| | |
|---|---|
| SiO2 | 46.0-72.0 |
| Li2O | 10.0-25.0 |
| ZrO2 | 6.5-14.0 |
| P2O5 | 1.0-10.0 |
| Al2O3 | 0.1-8.0 |
| K2O | 0.1-5.0 |
| CeO2 | 0.1-4.0 |
| B2O3 | 0.0-4.0 |
| Na2O | 0.0-4.0 |
| Tb4O7 | 0.0-2.5 | as well as 0.0 to 4.0 of at least one additive.

Preferably the composition of the glass-ceramic powder particles of the blank is (in % by weight):

| | |
|---|---|
| SiO2 | 49.0-69.0 |
| Li2O | 11.5-24.0 |
| ZrO2 | 7.0-13.5 |
| P2O5 | 1.5-9.0 |
| Al2O3 | 0.2-7.5 |
| K2O | 0.2-4.5 |
| CeO2 | 0.2-3.5 |
| B2O3 | 0.0-3.5 |
| Na2O | 0.0-3.5 |
| Tb4O7 | 0.0-2.0 | as well as 0.0 to 4.0 of at least one additive.

To be emphasized is a composition of the glass-ceramic powder particles for the blank of (in % by weight):

| | |
|---|---|
| SiO2 | 52.0-66.0 |
| Li2O | 12.0-22.5 |
| ZrO2 | 7.5-13.0 |
| P2O5 | 2.0-8.5 |
| Al2O3 | 0.3-7.0 |
| K2O | 0.3-4.0 |
| CeO2 | 0.3-3.5 |
| B2O3 | 0.0-3.0 |
| Na2O | 0.0-3.0 |
| Tb4O7 | 0.0-2.0 | as well as 0.0 to 4.0 of at least one additive.

Also to be emphasized is a composition of the glass-ceramic powder particles of the blank (in % by weight):

| | |
|---|---|
| SiO2 | 55.0-63.0 |
| Li2O | 12.5-21.5 |
| ZrO2 | 8.0-12.0 |
| P2O5 | 2.5-8.0 |
| Al2O3 | 0.4-6.5 |
| K2O | 0.4-4.0 |
| CeO2 | 0.5-3.0 |
| B2O3 | 0.0-3.0 |
| Na2O | 0.0-3.0 |
| Tb4O7 | 0.0-2.0 | as well as 0.0n to 4.0 of at least one additive.

Of particular note is a composition of the glass-ceramic powder particles for the blank of (in % by weight):

| | |
|---|---|
| SiO2 | 58.0-60.0 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0.0-3.0 |
| Na2O | 0.0-3.0 |
| Tb4O7 | 0.0-1.5 | as well as 0.0 to 4.0 of at least one additive.

The at least one additive is at least one additive selected out of the group containing colour pigment, fluorescent agent. In particular it is intended that the additive is at least one oxide selected from the group of BaO, CaO, MgO, MnO, Er2O3, Gd2O3, Pr6O11, Sm2O3, TiO2, V2O5, Y2O3 or contains such an oxide.

It should be noted that the total weight percentages of the components of the powder mixture in each composition add up to 100% by weight.

In particular, the invention also distinguishes itself by a process for producing a dental molded part, such as an inlay, onlay, crown, or bridge, comprising the procedural steps:

Producing a molten mass with a composition (in % by weight):

| | |
|---|---|
| SiO2 | 46.0-72.0 |
| Li2O | 10.0-25.0 |
| ZrO2 | 6.5-14.0 |
| P2O5 | 1.0-10.0 |
| Al2O3 | 0.1-8.0 |
| K2O | 0.1-5.0 |
| CeO2 | 0.1-4.0 |
| B2O3 | 0.0-4.0 |
| Na2O | 0.0-4.0 |
| Tb4O7 | 0.0-2.5 | as well as 0.0 to 4.0 of at least one additive.

Producing a glass frit by atomizing this molten mass and quenching in a medium,

If applicable, producing glass-powder particles from the glass frit, with a grain size distribution $d_{90} \leq 80$ μm, Crystallization of lithium silicate crystals with a volume fraction of between 10% and 90% by a first thermal treatment from either the glass frit or the glass powder particles in a first temperature range at a temperature $T_1$ with 500° C.$\leq T_1 \leq$750° C. for a duration $t_1$ with 5 min$\leq t_1 \leq$120 min, Whereby at a time when the glass frit has been subjected to a thermal treatment, one produces glass-ceramic particles with a grain size distribution $d_{90} \leq 80$ μm from the heat-treated glass frit, Pressing the glass-ceramic powder particles to form a blank, Machining the blank by milling to produce a pre-form part that corresponds to the dental molded part under consideration of the shrinkage characteristics of the blank, and Sintering the preformed part to completion at a temperature $T_2$ with 800° C.$\leq T_2 \leq$1050° C. for a time period $t_2$ with 5 min$\leq t_2 \leq$60 min.

The invention offers the choice between either subjecting the glass frit, without this having been ground to obtain glass-powder particles, to a thermal treatment for the formation of lithium silicate crystals, or at first grinding the frit, i.e. producing glass-powder particles, and carrying out the thermal treatment subsequently so that one obtains glass-ceramic particles. This means that the feature "Pressing the glass-ceramic powder particles to form a blank" consequently also comprises the glass-ceramic powder particles produced by the process alternatives.

In this, it is possible for the first thermal treatment to be implemented in two stages within the first temperature region.

In particular, the molten mass has a composition (in % by weight):

| | |
|---|---|
| SiO2 | 49.0-69.0 |
| Li2O | 11.5-24.0 |
| ZrO2 | 7.0-13.5 |
| P2O5 | 1.5-9.0 |
| Al2O3 | 0.2-7.5 |
| K2O | 0.2-4.5 |
| CeO2 | 0.2-3.5 |
| B2O3 | 0.0-3.5 |
| Na2O | 0.0-3.5 |
| Tb4O7 | 0.0-2.0 | as well as 0.0 to 4.0 of at least one additive.

The molten mass preferably has the following composition (in % by weight):

| | |
|---|---|
| SiO2 | 52.0-66.0 |
| Li2O | 12.0-22.5 |
| ZrO2 | 7.5-13.0 |
| P2O5 | 2.0-8.5 |
| Al2O3 | 0.3-7.0 |
| K2O | 0.3-4.0 |

-continued

| | |
|---|---|
| CeO2 | 0.3-3.5 |
| B2O3 | 0.0-3.0 |
| Na2O | 0.0-3.0 |
| Tb4O7 | 0.0-2.0 | as well as 0.0 to 4.0 of at least one additive.

To be particularly emphasized is a molten mass with a composition (in % by weight):

| | |
|---|---|
| SiO2 | 55.0-63.0 |
| Li2O | 12.5-21.5 |
| ZrO2 | 8.0-12.0 |
| P2O5 | 2.5-8.0 |
| Al2O3 | 0.4-6.5 |
| K2O | 0.4-4.0 |
| CeO2 | 0.5-3.0 |
| B2O3 | 0.0-3.0 |
| Na2O | 0.0-3.0 |
| Tb4O7 | 0.0-2.0 | as well as 0.0 to 4.0 of at least one additive.

The molten mass preferably has a composition (in % by weight):

| | |
|---|---|
| SiO2 | 58.0-60.0 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0.0-3.0 |
| Na2O | 0.0-3.0 |
| Tb4O7 | 0.0-1.5 | as well as 0.0 to 4.0 of at least one additive.

The at least one additive is at least one additive selected from the group of colour pigment, fluorescent agent. In particular it is intended that the additive is at least one oxide of the group BaO, CaO, MgO, MnO, Er2O3, Gd2O3, Pr6O11, Sm2O3, TiO2, V2O5, Y2O3, or contains such an oxide.

According to a further recommendation it is intended that the blank is tempered—after the first thermal treatment and prior to the machining—at a temperature $T_3$ with $750°$ C.$\leq T_3 \leq 900°$ C. for a time period $t_3$ with $5$ min$\leq t_3 \leq 30$ min.

The corresponding thermal treatment steps serve to ensure that the glass powder crystallizes to lithium silicate crystals on the required scale, and at the same time results in a small pore size and consequently dense packing of the grains, allowing a problem-free machining, which is also necessary to achieve filigree regions.

In this, the crystalline phase of lithium silicate includes lithium metasilicate and in particular lithium disilicate.

In particular, it is intended that for producing a blank with a disk-like geometry, the glass-ceramic powder particles are at first pressed axially and subsequently, after introduction into an encompassing element, such as a pouch coated by polyethylene on the inside, are subjected to isostatic re-pressing, whereby the re-pressing in particular takes place at a pressure pn of $250$ MPa$\leq pn \leq 350$ MPa for a time period $t_4$ with $5$ sec$\leq t_4 \leq 30$ sec, in particular $5$ sec$\leq t_4 \leq 15$ sec.

For producing a blank with cuboid geometry, the invention intends that the glass-ceramic powder particles are successively and in particular continuously axially pressed with rising pressure for a time period $t_5$, whereby the maximum pressure $p_5$ is $50$ MPa$\leq p_5 \leq 400$ MPa, in particular $100$ MPa$\leq p_5 \leq 200$ MPa. The duration of the pressure increase is $10$ sec$\leq t_5 \leq 20$ sec.

To produce a blank with rod-shaped, in particular cylindrical geometry, it is intended that the glass-ceramic powder is introduced into a tubular press form, in particular of polyurethane, and subsequently is subjected to quasi-isostatic pressing. The following pressing times and parameters should be taken into consideration for this. Preferably the pressure initially rises slowly, to distribute the filled glass-ceramic powder uniformly throughout the mold. After this, the pressure may be raised to its maximum value rapidly. Once the maximum pressure has been reached, it is maintained constant for the duration of the holding time. This is followed by a phase of rapid pressure release, during which the pressure is reduced to 10% of the maximum pressure value. Complete elimination of the excess pressure takes place slowly to prevent crack formation in the glass-ceramic blank.

With regard to the machining, which may be performed dry, it is in particular intended that an initial coarse machining is followed by precision machining.

Preferred machining parameters for the coarse machining are:

Cutter diameter: 2 to 5 mm, in particular 2 to 3 mm
Feed: 500 to 4000 mm/min, in particular 2000 to 3000 mm/min
Lateral feed ae: 0.2 to 3 mm, in particular 1 mm to 2 mm
Depth feed ap: 0.1 to 2 mm, in particular 0.5 mm to 1 mm
Cutter speed: 10,000 to 50,000 l/min, in particular 10,000 to 20,000 l/min.

The preferred cutters are carbide cutters.

With respect to the precision machining, the following machining parameters should be observed:
Cutter diameter: 0.3 to 1.5 mm, in particular 0.5 to 1.0 mm
Feed: 300 to 2000 mm/min, in particular 800 to 1500 mm/min
Lateral feed ae: 0.2 to 0.6 mm, in particular 0.1 mm to 0.2 mm
Depth feed ap: 0.05 to 0.3 mm, in particular 0.1 mm to 0.15 mm
Cutter speed: 20,000 to 60,000 l/min, in particular 25,000 to 35,000 l/min.

Here too, carbide cutters are preferrable.

Particularly good machining results are achieved when the employed cutter is a radius cutter of carbide, whereby the radius cutter should be characterized by the following cutting edge angles:
Cutting angle: $0°$ to $13°$, in particular $-9°$ to $-11°$
Clearance angle: $0°$ to $15°$, in particular $11°$ to $13°$
Wedge angle: Results from: $90°$ minus clearance angle minus cutting angle.

While in principle it is not necessary to add a binding agent prior to the pressing of the glass-ceramic particles, it is still within the scope of the invention if the corresponding binding agent, such as for example cellulose ether, is added with a weight fraction of up to 5%.

However it has been found to be particularly advantageous, if the blank, i.e. its glass-ceramic particles, after pressing are immersed in silicic acid or an alkali silicate solution (soluble glass) and after drying are subjected to the mechanical work. This causes SiO2 bridges to form between the glass particles, which increases rigidity and consequently simplifies the subsequent mechanical processing, which includes CAD/CAM processing. When the machined molded parts are sintered to completion, the free $SiO_2$ diffuses into the glass ceramic, which allows one to achieve an increase in rigidity.

The invention further distinguishes itself by a monolithic dental molded part, which is produced using the blank according to the invention. In particular, the monolithic dental molded part may constitute or comprise a crown with a crown margin of a thickness $D_R$ with $0.05$ mm $\leq D_R \leq 0.4$ mm, in particular $0.1$ mm $\leq D_R \leq 0.2$ mm. In this, the thickness of the crown margin extends starting at the front margin and at a distance of 2 to 4 mm to the latter.

The monolithic molded part is further characterized by a thermal expansion coefficient, measured in accordance with ISO6872, that is lower than $12.5 \times 10^{-6}$ 1/K, and preferably is between $9.5 \times 10^{-6}$ 1/K and $11.5 \times 10^{-6}$ 1/K.

For the pressing of the glass-ceramic particles, one in particular chooses a pressure between 50 MPa and 400 MPa, in particular between 100 MPa and 200 MPa. The temperature during the pre-sintering of the compacted glass powder, i.e. the blank in form of of the pressed glass body, should be in the range between 500° C. and 950° C., preferably between 600° C. and 700° C.

The external geometry of the pressed glass-ceramic body may be disk- or plate-like or rod-shaped such as cylindrical, whereby the cross-sectional geometry can be chosen freely. The volume content of the blanks may be between 1 cm³ and 160 cm³.

After the mechanical working of the blanks consisting of the crystalline porous glass ceramic, whereby this preferably is performed by milling without cooling, the carved-out dental works are subsequently sintered to completion in a suitable sintering furnace, taking into account a suitable temperature—time cycle. The sintering to completion may be performed in a temperature range between 700° C. and 1100° C., preferably in the range between 850° C. and 950° C. The duration of the entire cycle is less than 2 h, preferably less than 1 h. Because of the crystalline fraction it is not necessary to provide support for the pre-form part. Rather it is possible to place the pre-formed part onto an $Al_2O_3$ firing pad in the sintering furnace.

Parameters of the preferred temperature—time cycle are: Standby temperature 500° C., rate of increase 50° C./min to 90° C./min to 850 to 900° C., hold time 1 to 5 min, then slow cooling. For the cooling one preferably chooses the slowest cooling level.

Further details, advantages, and features of the invention are not only found in the claims and the characteristic features described therein—on their own and/or in combination—but also in the following exemplary embodiments.

FIG. 1 shows a graph of pressure versus time during the pressing of a blank.

In accordance with the invention, a blank consisting of pressed glass-ceramic powder is used to produce a dental molded part. To make the glass-ceramic powder, one at first melts a powder and uses the molten mass to produces a glass fit, which can possess the following preferred composition:

| | |
|---|---|
| SiO2 | 49.0-69.0 |
| Li2O | 11.5-24.0 |
| ZrO2 | 7.0-13.5 |
| P2O5 | 1.5-9.0 |
| Al2O3 | 0.2-7.5 |
| K2O | 0.2-4.5 |
| CeO2 | 0.2-3.5 |
| B2O3 | 0.0-3.5 |
| Na2O | 0.0-3.5 |
| Tb4O7 | 0.0-2.0 | as well as 0.0 to 4.0 of at least one additive.

In particular it is intended that the molten glass has a composition of (in % by weight):

| | |
|---|---|
| SiO2 | 49.0-69.0 |
| Li2O | 11.5-24.0 |
| ZrO2 | 7.0-13.5 |
| P2O5 | 1.5-9.0 |
| Al2O3 | 0.2-7.5 |
| K2O | 0.2-4.5 |
| CeO2 | 0.2-3.5 |
| B2O3 | 0.0-3.5 |
| Na2O | 0.0-3.5 |
| Tb4O7 | 0.0-2.0 | as well as 0.0 to 4.0 of at least one additive.

Preferably the molten glass has a composition of (in % by weight):

| | |
|---|---|
| SiO2 | 52.0-66.0 |
| Li2O | 12.0-22.5 |
| ZrO2 | 7.5-13.0 |
| P2O5 | 2.0-8.5 |
| Al2O3 | 0.3-7.0 |
| K2O | 0.3-4.0 |
| CeO2 | 0.3-3.5 |
| B2O3 | 0.0-3.0 |
| Na2O | 0.0-3.0 |
| Tb4O7 | 0.0-2.0 | as well as 0.0 to 4.0 of at least one additive.

Especially emphasized is a composition of the molten glass with a composition (in % by weight) of:

| | |
|---|---|
| SiO2 | 55.0-63.0 |
| Li2O | 12.5-21.5 |
| ZrO2 | 8.0-12.0 |
| P2O5 | 2.5-8.0 |
| Al2O3 | 0.4-6.5 |
| K2O | 0.4-4.0 |
| CeO2 | 0.5-3.0 |
| B2O3 | 0.0-3.0 |
| Na2O | 0.0-3.0 |
| Tb4O7 | 0.0-2.0 | as well as 0.0 to 4.0 of at least one additive.

Preferably it is intended that the molten glass has a composition (in % by weight) of:

| | |
|---|---|
| SiO2 | 58.0-60.0 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0.0-3.0 |
| Na2O | 0.0-3.0 |
| Tb4O7 | 0.0-1.5 | as well as 0.0 to 4.0 of at least one additive.

The at least one additive is at least one additive selected from the group composed of colour pigment, fluorescent agent. In particular it is intended that the additive is at least one oxide chosen from the group of BaO, CaO, MgO, MnO, Er2O3, Gd2O3, Pr6O11, Sm2O3, TiO2, V2O5, Y2O3 or contains such an oxide.

The corresponding mixture of starting materials, e.g. in form of oxides and carbonates, subsequently is melted in a suitable crucible of refractory material or a noble metal alloy at a temperature between 1350° C. and 1600° C. for a time period between 1 h and 10 h, in particular for a time of 4 h to 7 h at a temperature of 1540° C. Homogenization is achieved, e.g. by stirring, at the same time or subsequently. The liquid glass produced in this manner subsequently is fed to a nozzle, which preferably has been caused to oscillate, and which itself is set to a temperature in the region between 1250° C. and 1450° C., in particular to 1310° C. The nozzle may possess a diameter between 1 mm and 2 mm. The oscillation frequency of the nozzle may be in the range between 40 Hz and 60 Hz, in particular in the region of 50 Hz. Subsequently the liquid glass is quenched in a suitable medium, such as water for liquids or high-temperature insulation wool. The glass frit produced and quenched in this manner is then dried. This is followed by grinding e.g. in a ball mill. A subsequent sifting stage can use a screen with a mesh width between 50 μm and 500 μm. If required, a further grinding can be performed, e.g. using a jet mill or an attrition mill.

From the glass- or glass-particle powder produced in this manner, one in particular selects those that correspond to a grain size distribution of $d_{90} \leq 80$ μm, in particular $10$ μm$\leq d_{50} \leq 60$ μm. $d_{90}$ and $d_{50}$ indicate that 90% or 50%, respectively, of the particles present possess a diameter that is smaller than the specified value or that is in that particular region.

In order to facilitate easy machining of the blank, without risking any instabilities during the final sintering of the molded part produced from blank, one subjects either the frit obtained after melting or the pre-ground or completely ground powder to a crystallization step. In this, one subjects the frit or the powder in a first thermal treatment step to a temperature $T_1$ between 500° C. and 750° C. for a duration $t_1$ between 5 min and 120 min. The first thermal treatment step may also be implemented as a two-stage process, i.e. first thermal treatment step 640° C., preferably 660° C. for 60 min and 750° C. for 40 min.

Preferably this is followed by a further thermal treatment in form of tempering, whereby the temperature $T_3$ to be selected should be between 750° C. and 900° C. This tempering step is performed for a duration $t_3$, in particular between 5 min and 30 min.

Subsequently the glass-ceramic particles are pressed, where in dependence on the geometry to be produced, one uses suitable pressing methods, in particular an axial or isostatic pressing or combinations of these. The compressing is carried out to such a degree that the density of the blank corresponds to 30% to 60% of the theoretical density of the blank material of approximately 2.64 g/cm³. In particular, the blank should possess a density corresponding to approximately 50% of the theoretical density.

During the pressing of the glass-ceramic powder, the latter preferably is subjected to a pressure between 50 MPa and 400 MPA, in particular between 100 MPa and 200 MPa.

FIG. 1 shows as an example a graph of pressure versus time during the pressing of a blank. In a first phase P1 the pressure is increased from a starting value of 0 with a pressure build-up of for example 15 MPa/sec to a pressure of for example 30 MPa. In a second phase P2 the pressure is increased from 30 MPa using a pressure build-up of 100 MPa/sec to a pressure of approximately 200 MPa. In a third phase P3 the pressure is kept constant at a value of approximately 200 MPa for a hold time of approximately 10 sec. A fourth phase preferably contains a two-stage pressure reduction, whereby in a phase P4a the pressure is reduced from approximately 200 MPa to approximately 20 MPa with a pressure-reduction of 40 MPa/sec and in a phase P4b the pressure is reduced from 20 MPa to 0 MPa excess pressure with a pressure reduction rate of approximately 10 MPa/sec.

The pressing is followed by machining by means of milling, whereby it is possible to at first perform a coarse machining, to be followed by precision machining. The machining may be performed without cooling, which allows dry machining.

The following milling parameters should be taken into account for the coarse machining:
Cutter diameter: 1 to 5 mm, in particular 2 to 3 mm
Feed: 500 to 4000 mm/min, in particular 2000 to 3000 mm/min
Lateral feed ae: 0.2 to 3 mm, in particular 1 mm to 2 mm
Depth feed ap; 0.1 to 2 mm, in particular 0.5 mm to 1 mm
Cutter speed: 10,000 to 50,000 l/min, in particular 10,000 to 20,000 l/min In particular, the milling tool should be a carbide cutter.
Milling parameters to be considered for the precision machining:
Cutter diameter: 0.3 to 1.5 mm, in particular 0.5 to 1.0 mm
Feed: 300 to 2000 mm/min, in particular 800 to 1500 mm/min
Lateral feed ae: 0.2 to 0.6 mm, in particular 0.1 mm to 0.2 mm
Depth feed ap: 0.05 to 0.3 mm, in particular 0.1 mm to 0.15 mm
Cutter speed: 20,000 to 60,000 l/min, in particular 25,000 to 35,000 l/min In particular, the milling tool should be a carbide cutter.
Preferably one uses a radius cutter of carbide that may be coated with titanium nitride. In this, the following cutting edge angles represent preferred values:
Cutting angle: 0° to −13°, in particular −9° to −11°
Clearance angle: 0° to 15°, in particular 11° to 13°
Wedge angle: results from: 90° minus clearance angle minus cutting angle Because of the density of the blank and the crystalline fraction, it becomes possible to easily produce dental molded parts with filigree edges. For crowns in particular, it has been found that this results in stably extending edge thicknesses between 0.05 mm and 0.4 mm.

After the cutting work, the molded part created from the blank should be referred to as pre-form part, since it exhibits an oversize compared to the dental molded part after complete sintering in accordance with the shrinkage characteristic of the blank material. The oversize is calculated in dependence on the density of the blank, in order to provide a high-precision dental prostheses after the final sintering.

The sintering to final density takes place at a temperature $T_2$ between 800° C. and 1050° C. for the duration of a holding time $t_2$ between 5 min and 60 min. Holding time in this regard means that the blank is kept at this temperature during the final sintering stage.

For the final sintering, the pre-form part is arranged on a fire-proof base, such as firing pads, or on free-of-scale metal layers. Support structures are not required, since the dimensional stability is guaranteed by the preceding crystallisation of the original powder material.

The following exemplary embodiments illustrate further characteristic features of the invention, whereby the listed parameters are of particular significance on their own but not necessarily in combination:

1. Producing a Disk-Shaped Blank

A quantity of 230 g pre-crystallized glass-ceramic powder, which also contains lithium silicate crystal, with a composition (in % by weight):

| | |
|---|---|
| SiO2 | 58-60 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0-3 |
| Na2O | 0-3 |
| Tb4O7 | 0-1.5 | as well as 0 to 4 of at least one additive, with a grain size distribution of $d_{50}=18.7$ μm are pre-compacted at a pressure of 50 MPa by means of a tool with a diameter of 105 mm using a hydraulic press. Subsequently the pellet is introduced into a PE-coated pouch, which is evacuated and sealed watertight. The pellet is subjected to an isostatic re-compression at 290 MPa for 10 sec in a water-oil emulsion. The unpacking is followed by a thermal treatment and a partial sintering at 650° C. The blank density is 1.88 g/cm$^3$.

The final geometry of the blank is created by lathing to an outside diameter of 98.5 mm. A recess is lathed on each of the two front ends to facilitate acceptance into a milling machine.

Into the blank surface with a circular geometry one nests dental molded parts with an appropriate sintering oversize. If crowns are the chosen molded part, they exhibit an excellent and fine crown margin and an outstanding milling surface.

Sintering takes place in a dental furnace on Al$_2$O$_3$ firing pads with a multi-step sintering program over a total duration of 60 min. A multi-stage sintering program in this context means that holding times are provided for at least two different temperatures, so that these temperatures are maintained constant for the duration of the respective holding times. The maximum sintering temperature was 950° C., and was kept for a duration of 10 min. The subsequent evaluation of the crowns revealed an aesthetic visual appearance with a good dental fit.

2. Producing a Cuboid Blank

A quantity of 9.6 g of pre-crystallized glass-ceramic powder with a composition (in % by weight):

| | |
|---|---|
| SiO2 | 58-60 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0-3 |
| Na2O | 0-3 |
| Tb4O7 | 0-1.5 | as well as 0 to 4 of at least one additive, with a grain size distribution of $d_{50}=21.3$ μm is axially compressed under continuously rising pressure up to 120 MPa using a hydraulic press in a carbide press mould and is demolded under a suitable load of preferably 5 MPa. The resulting pellet possesses dimensions of 20.2×19.1×15.9 mm and a density of 1.56 g/cm$^3$. Subsequently the pellet is subjected to two-stage thermal treatment at 630° C. and 700° C. in an elevator furnace. The blank density after the thermal treatment rose to 1.75 g/cm$^3$.

A mushroom-shaped adapter is glued to the narrow side of the blank to facilitate acceptance into a processing machine. The carving work on the dental crown that was oversized to compensate for sintering shrinkage took place using a special speed milling operation with significantly reduced cutting time using a cutting feed of up to 2000 mm/min. This represents a significant shortening of the cutting time in comparison to the part produced in example 1. The crown exhibited a smooth exterior and the crown margin was free from break-outs. The sintering took place on Al$_2$O$_3$ firing pads in a dental furnace with a stepped cycle with a total duration of 65 min and a maximum sintering temperature of 950° C. for 10 min. A subsequent evaluation of the crown revealed an aesthetic colour and a good dental fit.

3. Producing a Rod-Shaped Blank

A quantity of 210 g of pre-crystallized glass-ceramic powder with a composition (in % by weight) of:

| | |
|---|---|
| SiO2 | 58-60 |
| Li2O | 13.5-20.5 |
| ZrO2 | 8.5-11.5 |
| P2O5 | 3.0-7.5 |
| Al2O3 | 0.5-6.0 |
| K2O | 0.5-3.5 |
| CeO2 | 0.5-2.5 |
| B2O3 | 0-3 |
| Na2O | 0-3 |
| Tb4O7 | 0-1.5 | as well as 0 to 4 of at least one additive, with a grain size distribution of $d_{50}=19.1$ μm is compressed using a wet-bag press at a quasi-isostatic pressure of 195 MPa in a tubular polyurethane mould. The demolding is followed by a thermal treatment for additional crystallization at 620° C. and pre-sintering at 680° C. The final blank geometry is created by lathing to an outside diameter of 25 mm and a length of 198 mm. The blank possesses a density of 1.81 g/cm$^3$ From the face of rod-shaped glass-ceramic blanks one cuts dental crowns with an appropriate sintering oversize. The crowns possess a narrow crown margin free of break-outs and a good cutting surface. Sintering takes place in a small batch furnace on trays with Al$_2$O$_3$ firing pads. One employs a sintering program with an overall cycle time of 45 min. The maximum temperature of the sintering treatment is 980° C. The blank was kept at this temperature for 5 min. The completed crowns exhibit an aesthetic visual appearance and a good dental fit.

The invention claimed is:

1. A blank for producing a dental molded part, the blank comprising:
  pre-crystalized glass-ceramic powder particles having lithium silicate crystals; and
  wherein the blank has a density between 30% and 60% of a theoretical density of a fully-sintered blank; and
  wherein the blank is formed from the pre-crystalized glass-ceramic powder particles having a grain size distribution $d_{50} \leq 25$ μm; and
  wherein a fraction of lithium silicate crystals is between 10% by volume and 90% by volume and wherein: the blank possesses a disk-, cube-, or rod-shaped geometry, and means for arrangement in a milling machine originating from the circumferential surface of the blank and extending diametrically relative to the center of gravity.

2. The blank of claim 1, wherein: the blank possesses an open porosity between 5% by volume and 60% by volume.

3. A blank for producing a dental molded part, the blank comprising:
   pre-crystalized glass-ceramic powder particles having lithium silicate crystals;
   wherein the blank has a density between 30% and 60% of a theoretical density of a fully-sintered blank; and
   the pre-crystalized glass-ceramic powder particles having a grain size distribution $d_{90} \leq 80$ µm;
   wherein a fraction of lithium silicate crystals is between 10% by volume and 90% by volume and wherein the pre-crystalized glass-ceramic powder particles possess a composition in % by weight:
   $SiO_2$ 46.0-72.0;
   $Li_2O$ 10.0-25.0;
   $ZrO_2$ 6.5-14.0;
   $P_2O_5$ 1.0-10.0;
   $Al_2O_3$ 0.1-8.0;
   $K_2O$ 0.1-5.0;
   $CeO_2$ 0.1-4.0;
   $B_2O_3$ 0.0-4.0;
   $Na_2O$ 0.0-4.0;
   $Tb_4O_7$ 0.0-2.5; and
   0.0 to 4.0 of at least one additive.

4. The blank of claim 1, wherein the pre-crystalized glass-ceramic powder particles possess a composition in % by weight:
   $SiO_2$ 49.0-69.0;
   $Li_2O$ 11.5-24.0;
   $ZrO_2$ 7.0-13.5;
   $P_2O_5$ 1.5-9.0;
   $Al_2O_3$ 0.2-7.5;
   $K_2O$ 0.2-4.5;
   $CeO_2$ 0.2-3.5;
   $B_2O_3$ 0.0-3.5;
   $Na_2O$ 0.0-3.5;
   $Tb_4O_7$ 0.0-2.0; and
   0.0 to 4.0 of at least one additive.

5. The blank of claim 4, wherein the pre-crystalized glass-ceramic powder particles possess a composition in % by weight:
   $SiO_2$ 52.0-66.0;
   $Li_2O$ 12.0-22.5;
   $ZrO_2$ 7.5-13.0;
   $P_2O_5$ 2.0-8.5;
   $Al_2O_3$ 0.3-7.0;
   $K_2O$ 0.3-4.0;
   $CeO_2$ 0.3-3.5;
   $B_2O_3$ 0.0-3.0;
   $Na_2O$ 0.0-3.0;
   $Tb_4O_7$ 0.0-2.0; and
   0.0 to 4.0 of at least one additive.

6. The blank of claim 3, wherein the pre-crystalized glass-ceramic powder particles possess a composition in % by weight of:
   $SiO_2$ 55.0-63.0;
   $Li_2O$ 12.5-21.5;
   $ZrO_2$ 8.0-12.0;
   $P_2O_5$ 2.5-8.0;
   $Al_2O_3$ 0.4-6.5;
   $K_2O$ 0.4-4.0;
   $CeO_2$ 0.5-3.0;
   $B_2O_3$ 0.0-3.0;
   $Na_2O$ 0.0-3.0;
   $Tb_4O_7$ 0.0-2.0; and
   0.0 to 4.0 of at least one additive.

7. The blank of claim 1, wherein the pre-crystalized glass-ceramic powder particles possess a composition in % by weight:
   $SiO_2$ 58-60;
   $Li_2O$ 13.5-20.5;
   $ZrO_2$ 8.5-11.5;
   $P_2O_5$ 3.0-7.5;
   $Al_2O_3$ 0.5-6.0;
   $K_2O$ 0.5-3.5;
   $CeO_2$ 0.5-2.5;
   $B_2O_3$ 0-3;
   $Na_2O$ 0-3;
   $Tb_4O_7$ 0-1.5; and
   0.0 to 4.0 of at least one additive.

8. The blank of claim 3, wherein: the additive is selected from the group consisting of: color pigment, and fluorescent agent.

9. The blank of claim 3, wherein: the additive comprises at least one oxide selected from the group consisting of BaO, CaO, MgO, MnO, $Er_2O_3$, $Gd_2O_3$, $Pr_6O_{11}$, $Sm_2O_3$, $TiO_2$, $V_2O_5$, and $Y_2O_3$.

10. The blank of claim 1, wherein: the fraction of lithium silicate crystals is between 40% by volume and 60% by volume.

11. A method for producing a dental molded part, the method comprising the steps of:
    producing a molten mass with a composition (in % by weight):
    $SiO_2$ 46.0-72.0;
    $Li_2O$ 10.0-25.0;
    $ZrO_2$ 6.5-14.0;
    $P_2O_5$ 1.0-10.0;
    $Al_2O_3$ 0.1-8.0;
    $K_2O$ 0.1-5.0;
    $CeO_2$ 0.1-4.0;
    $B_2O_3$ 0.0-4.0;
    $Na_2O$ 0.0-4.0;
    $Tb_4O_7$ 0.0-2.5; and
    0.0 to 4.0 of at least one additive,
    producing a glass frit by atomizing the molten mass and quenching the molten mass in a medium,
    generating glass powder particles from the glass frit with a grain size distribution $d_{90} < 80$ µm,
    crystallizing lithium silicate crystals with a volume fraction between 10% and 90% by a first thermal treatment of either the glass frit or the glass powder particles in a first temperature range at a temperature $T_1$ with 500° C.$\leq T_1 \leq$750° C. for a duration $t_1$ with 5 min$\leq t_1 \leq$120 min, whereby, glass-ceramic powder particles with a grain size distribution $d_{90} \leq 80$ µm are produced from a heat-treated glass frit,
    pressing the glass-ceramic powder particles to form a blank,
    machining the blank by milling to produce a pre-form part corresponding to the dental molded part, taking into consideration the shrinkage characteristics of the blank, and
    sintering the pre-form part at a temperature $T_2$ with 800° C.$\leq T_2 \leq$1050° C. for a duration $t_2$ with 5 min$\leq t_2 \leq$60 min.

12. The method of claim 11, wherein the molten mass comprises (in % by weight):
    $SiO_2$ 49.0-69.0;
    $Li_2O$ 11.5-24.0;

ZrO$_2$ 7.0-13.5;
P$_2$O$_5$ 1.5-9.0;
Al$_2$O$_3$ 0.2-7.5;
K$_2$O 0.2-4.5;
CeO$_2$ 0.2-3.5;
B$_2$O$_3$ 0.0-3.5;
Na$_2$O 0.0-3.5;
Tb$_4$O$_7$ 0.0-2.0; and
0.0 to 4.0 of at least one additive.

13. The method of claim 11, wherein the molten mass comprises (in % by weight):
SiO$_2$ 52.0-66.0;
Li$_2$O 12.0-22.5;
ZrO$_2$ 7.5-13.0;
P$_2$O$_5$ 2.0-8.5;
Al$_2$O$_3$ 0.3-7.0;
K$_2$O 0.3-4.0;
CeO$_2$ 0.3-3.5;
B$_2$O$_3$ 0.0-3.0;
Na$_2$O 0.0-3.0;
Tb$_4$O$_7$ 0.0-2.0; and
0.0 to 4.0 of at least one additive.

14. The method of claim 11, wherein the molten mass comprises (in % by weight):
SiO$_2$ 55.0-63.0;
Li$_2$O 12.5-21.5;
ZrO$_2$ 8.0-12.0;
P$_2$O$_5$ 2.5-8.0;
Al$_2$O$_3$ 0.4-6.5;
K$_2$O 0.4-4.0;
CeO$_2$ 0.5-3.0;
B$_2$O$_3$ 0.0-3.0;
Na$_2$O 0.0-3.0;
Tb$_4$O$_7$ 0.0-2.0; and
0.0 to 4.0 of at least one additive.

15. The method of claim 11, wherein the molten mass comprises (in % by weight):
SiO$_2$ 58-60;
Li$_2$O 13.5-20.5;
ZrO$_2$ 8.5-11.5;
P$_2$O$_5$ 3.0-7.5;
Al$_2$O$_3$ 0.5-6.0;
K$_2$O 0.5-3.5;
CeO$_2$ 0.5-2.5;
B$_2$O$_3$ 0-3;
Na$_2$O 0-3;
Tb$_4$O$_7$ 0-1.5; and
0.0 to 4.0 of at least one additive.

16. The method of claim 11, wherein: prior to machining and after the first thermal treatment, the blank is tempered at a temperature T$_3$ with 750° C.≤T$_3$≤900° C. for a duration t$_3$ with 5 min≤t$_3$≤30 min.

17. The method of claim 11, wherein: to produce a blank with a disk geometry, the glass-ceramic powder particles are first axial pressed and subsequently, upon insertion into an encasing element such as a pouch coated with polyethylene on its inside, are subjected to isostatic re-compression, whereby the re-compression in particular is performed at a pressure p$_n$ with 250 MPa≤p$_n$≤350 MPa for a time t$_4$ with 5 sec≤t$_4$≤30 sec.

18. The method of claim 11, wherein: for the production of a blank with a cube geometry, the glass-ceramic powder particles are axially pressed successively and in particular continuously with increasing pressure for a duration t$_5$ with 10 sec≤t$_5$≤20 sec, whereby the maximum pressure is p$_5$, with 50 MPa≤p$_5$≤400 MPa.

19. The method of claim 11, wherein: for the production of a rod-shaped blank, the glass-ceramic powder is introduced into a tubular press mould and subsequently is subjected to quasi-isostatic pressing.

20. The method of claim 11, wherein:
the blank is subjected to at least a coarse machining by milling and subsequent precision machining, whereby milling parameters for the coarse machining comprise:
Cutter diameter: 2 to 5 mm,
Feed: 500 to 4000 mm/min,
Lateral feed ae: 0.2 to 3 mm,
Depth feed ap: 0.1 to 2 mm,
Cutter speed: 10.000 to 50.000 1/min,
the milling parameters for the precision machining comprise:
Cutter diameter: 0.3 to 1.5 mm,
Feed: 300 to 2000 mm/min,
Lateral feed ae: 0.2 to 0.6 mm,
Depth feed ap: 0.05 to 0.3 mm,
Cutter speed: 20,000 to 60,000 1/min.

21. The method of claim 20, wherein: the cutter is a radius cutter with the following cutting edge angles:
Cutting angle: 0° to −13°,
Clearance angle: 0° to 15°,
Wedge angle: Results from: 90° minus clearance angle minus cutting angle.

22. The method of claim 11, wherein: the blank is immersed in silicic acid or in an alkali silicate solution, is dried, and subsequently is machined by dry milling, or in that the blank is machined by milling and subsequently, prior to the sintering to the final density, is immersed in silicic acid or alkali silicate solution and subsequently dried.

23. A monolithic dental molded part manufactured in accordance with the method of claim 11 using a blank comprising lithium silicate crystals and one or more glass ceramics with a density between 30% and 60% of a theoretical density of a fully-sintered blank, wherein the blank is formed from glass-ceramic powder particles with a grain size distribution d$_{90}$≤80 μm and wherein a fraction of lithium silicate crystals is between 10% by volume and 90% by volume; and wherein: the dental molded part comprises a crown and possesses a crown margin with a thickness D$_R$ of 0.05 mm≤D$_R$≤0.4 mm.

24. The monolithic dental molded part of claim 23, wherein: the molded part has a thermal expansion coefficient WAK with WAK≤12.5×10$^{-6}$ 1/K.

* * * * *